US007824729B2

(12) United States Patent
Roorda et al.

(10) Patent No.: US 7,824,729 B2
(45) Date of Patent: Nov. 2, 2010

(54) METHODS FOR COATING AN IMPLANTABLE DEVICE

(75) Inventors: Wouter E. Roorda, Palo Alto, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/043,926

(22) Filed: Mar. 6, 2008

(65) Prior Publication Data

US 2008/0213462 A1 Sep. 4, 2008

Related U.S. Application Data

(60) Division of application No. 10/894,897, filed on Jul. 19, 2004, now abandoned, which is a continuation of application No. 09/966,420, filed on Sep. 27, 2001, now abandoned.

(51) Int. Cl.
*A61L 33/00* (2006.01)

(52) U.S. Cl. ...................... 427/2.24; 118/620; 118/600; 118/303; 118/19; 427/212; 427/215; 427/242; 427/421; 427/555

(58) Field of Classification Search ................. 118/303, 118/600, 620; 427/2.24; 623/1.1
See application file for complete search history.

(56) References Cited

U.S. PATENT DOCUMENTS 3,357,398 A 12/1967 Gross
3,841,262 A 10/1974 Groppenbacher et al.
3,911,860 A 10/1975 Nohynek
4,141,316 A 2/1979 Grun
4,176,591 A 12/1979 Power
4,576,108 A 3/1986 Socola et al.
4,581,242 A 4/1986 Forster
4,639,383 A 1/1987 Casey
4,685,419 A * 8/1987 Nakajima .................. 118/620
4,688,514 A 8/1987 Yamabayashi et al.
4,733,665 A 3/1988 Palmaz
4,800,882 A 1/1989 Gianturco
4,886,062 A 12/1989 Wiktor
4,952,419 A 8/1990 De Leon et al.
5,158,804 A 10/1992 Alkan et al.
5,338,569 A 8/1994 Hatch
5,370,734 A 12/1994 Ferrero
5,376,175 A * 12/1994 Long et al. .................. 118/303
5,863,614 A 1/1999 Williamitis et al.
6,129,038 A 10/2000 Morrow et al.
6,214,407 B1 4/2001 Laube et al.
6,254,888 B1 7/2001 Cappola
6,258,799 B1 7/2001 Kokubo et al.

(Continued)

FOREIGN PATENT DOCUMENTS

DE 3420859 12/1985

(Continued)

*Primary Examiner*—Michael Barr
*Assistant Examiner*—Andrew Bowman
(74) *Attorney, Agent, or Firm*—Squire, Sanders & Dempsey L.L.P.

(57) ABSTRACT

A process for coating an implantable device is disclosed. In this process, at least one implantable device is tumbled. As the implantable device is being tumbled, a coating substance is introduced to coat the implantable device with the coating substance.

8 Claims, 2 Drawing Sheets

U.S. PATENT DOCUMENTS

| | | | | |
|---|---|---|---|---|
| 6,364,948 | B1 | 4/2002 | Austin et al. | |
| 6,368,658 | B1 | 4/2002 | Schwarz et al. | |
| 6,607,598 | B2 | 8/2003 | Schwarz et al. | |
| 2002/0110689 | A1 | 8/2002 | Hu et al. | |
| 2002/0122877 | A1 * | 9/2002 | Harish et al. | 427/2.24 |
| 2003/0165614 | A1 | 9/2003 | Hansen et al. | |
| 2004/0181271 | A1 * | 9/2004 | DeSimone et al. | 623/1.1 |

FOREIGN PATENT DOCUMENTS

| | | | |
|---|---|---|---|
| WO | WO 00/62830 | * | 10/2000 |
| WO | WO0062830 | * | 10/2000 |

* cited by examiner

METHODS FOR COATING AN IMPLANTABLE DEVICE

This application claim priority under 35 U.S.C. §120 as a divisional of U.S. application Ser. No. 10/894,897 filed Jul. 19, 2004, now abandoned which is a continuation of U.S. application Ser. No. 09/966,420, filed Sep. 27, 2001, now abandoned.

BACKGROUND

This invention relates to processes for coating an implantable device or an endoluminal prosthesis, such as, for example, a stent.

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents may be used not only as a mechanical intervention but also as a vehicle for providing biological therapy. As a mechanical intervention, stents may act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty; restenosis, however, is still a significant clinical problem. When restenosis does occur in the stented segment, its treatment can be challenging, as clinical options are more limited as compared to lesions that were treated solely with a balloon.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Although stents work well mechanically, the chronic issues of restenosis and, to a lesser extent, stent thrombosis remain. These events are affected by, and made worse, by mechanical aspects of the stent such as the degree of injury and disturbance of hemodynamics. To the extent that the mechanical functionality of stents has been optimized, it has been postulated that continued improvements could be made by pharmacological therapies. Many systemic therapies have been tried. A challenge is maintaining the necessary concentration of drug at the lesion site for the necessary period of time. This can be done via brute force methods using oral or intravenous administration but the issues of systemic toxicity and side effects arise. Therefore, a preferred route may be achieved by local delivery of drug from the stent itself. Stents are composed of struts that are typically 50-150 microns wide. Being made of metal, plain stents are not useful for drug delivery. Therefore, a coating, usually of a polymer, is applied to serve as a drug reservoir.

Slotted tube stents are made by laser cutting a solid metal hypotube. Leading stent manufacturers can produce thousands of stents per day. Consequently, the drug coating process, which is added on to the existing stent manufacturing process, needs to be rapid and reproducible. Stents are difficult to coat evenly due to their intricate geometry and small size. Conventional coating techniques fill in the spaces between struts creating webbing and bridging. A versatile method of stent coating is by a spray process that avoids webbing by the application of small droplets.

In order to coat a stent, it typically must be held in some manner. This allows it to be positioned and moved under a spray nozzle in a controlled and repeatable manner. However, holding a stent requires making contact with it. At these contact points, the liquid coating can web, accumulate or wick. After drying, this leads to thick coating deposits at the contacts between the stent and the fixture. These deposits can also attach the stent to the holding fixture, which creates tearing and bare spots when the two are eventually separated. It is desirable that the stent be completely coated on all surfaces with no significant bare spots. It is also desirable that there be no significant defects associated with the fixturing. It is further desirable that a coating process is capable of allowing the coating of a large amount or number of stents at one time.

SUMMARY OF THE INVENTION

A process for coating an implantable device is disclosed. In this process, at least one implantable device is tumbled. As the implantable device is being tumbled, a coating substance is introduced to coat the implantable device with the coating substance.

In one embodiment, the implantable device is a stent. In another embodiment, the implantable device may be tumbled in a pan. In a further embodiment, the implantable device may be tumbled about a rotating axis extending at an angle between 0 degrees and 90 degrees with respect to a horizontal plane. As an option in such an embodiment, the rotating axis may extend at about 45 degrees with respect to the horizontal plane. In yet another embodiment, the rotating axis may be rotated between about 5 revolutions per minute (rpm) and about 400 rpm.

In one embodiment, coating substance may be sprayed on to the tumbling implantable device. The coating substance may be sprayed on to the tumbling implantable device for a duration of between about 1 minute and about 120 minutes. In an embodiment of the present invention, the coating substance may include a polymer dissolved in a fluid and optionally, an active agent added thereto.

In yet another embodiment, a gaseous composition may be directed over the tumbling implantable device to aid in the drying of the coating substance. In one such embodiment, the gaseous composition may comprise air. The gaseous composition may have a temperature between about 15° C. and 200° C.

DETAILED DESCRIPTION

Figure 1:
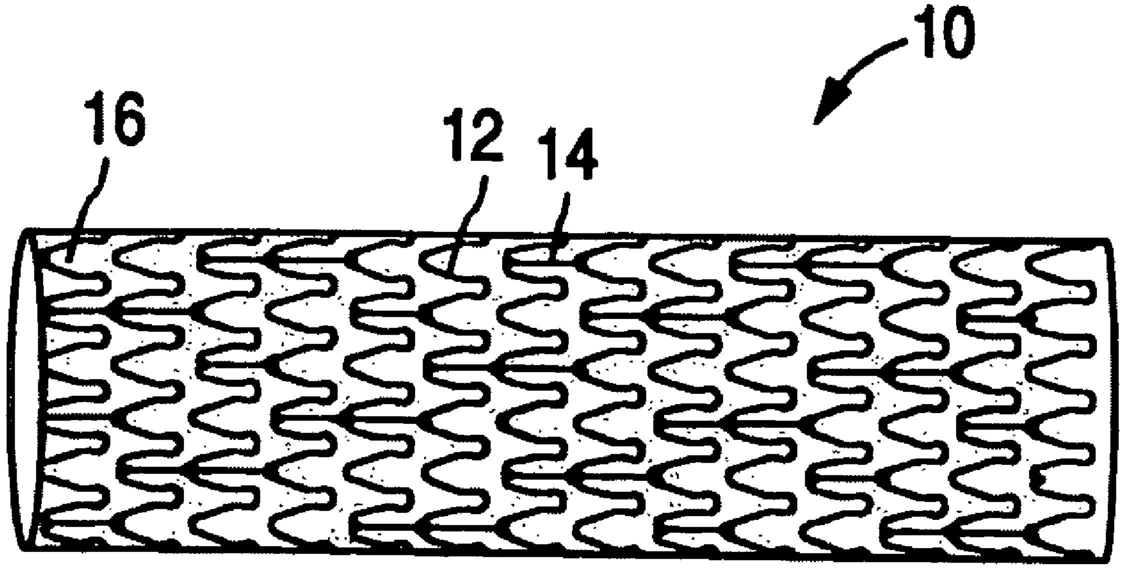
FIG. 1 illustrates a conventional stent.
Figure 2:
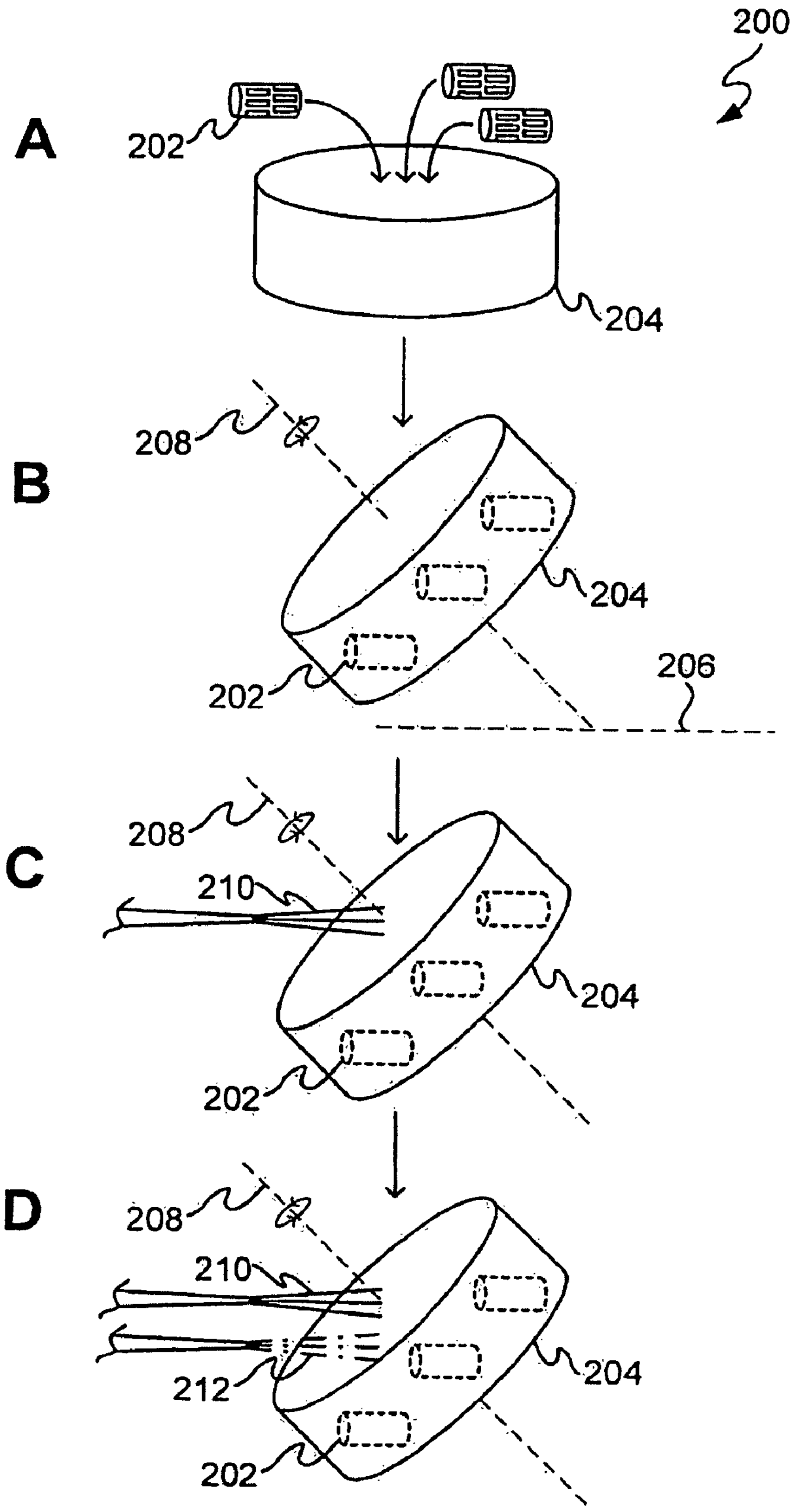
FIG. 2 is a schematic flow diagram illustrating a process for coating an implantable device in accordance with an embodiment of the present invention.

FIG. 2 is a schematic flow diagram illustrating a general overview of a process 200 for coating an implantable device, such as a stent, in accordance with an embodiment of the present invention. At least one stent 202 is deposited in a pan 204 (see A of FIG. 2).

The pan 204 is agitated to tumble the stent(s) 202 in the pan 204 (see B of FIG. 2). Agitation of the pan 204 may be achieved utilizing a variety of modes including, but not limited to, shaking of the pan 204 to tumble the stent(s) 202 therein. As illustrated in FIG. 2, in one embodiment, agitation of the pan 204 may be achieved by tilting the pan 204 with respect to a horizontal plane 206 such that an axis 208 of the pan 204 extends at an acute angle (e.g., extending at an angle between 0 degrees and 90 degrees) to the horizontal plane 206. The pan 204 can be rotated about the axis 208 to tumble the stent(s) 202 in the pan 204. As an option, the rotating axis 208 may extend at about 45 degrees with respect to the horizontal plane 206. In one embodiment, the pan 204 may be rotated between about 5 revolutions per minute (rpm) and about 400 rpm and in a preferred embodiment between about 10 rpm and about 200 rpm.

Continuing the process 200, a coating substance is introduced to coat the tumbling stent(s) 202. In one embodiment, the coating substance 210 may be sprayed into the pan 204 to coat the tumbling stent(s) 202 with the coating substance (see C of FIG. 2). Because of the continuous tumbling motion, the spray coating solution is divided equally over the stents 202. In one embodiment, the coating substance may comprise a polymer dissolved in a fluid and, optionally, an active agent added thereto. The actual spray time chosen may depend on various factors such as, for example, the equipment used, the number of stents being deposited in the pan 204, and the volatility of the solvent.

As a further option, gaseous composition 212 may be directed over the tumbling stent(s) 202 to aid in the drying of the coating substance on the stent(s) 202. In the embodiment illustrated in FIG. 2, the gaseous compound 212 may be blown into the rotating pan 204 to aid drying of the coating substance 210 on the tumbling stent(s) 202 (see D of FIG. 2). In one such embodiment, the gaseous composition 212 may comprise air. As another option, the gaseous composition 212 may have a temperature between about 15° C. and about 200° C.

It should further be noted that one or more subsequent coating substances may also be sequentially introduced to the tumbling implantable device to apply one or more further coatings on the implantable device.

Embodiments of the disclosed process may be utilized to coat one or more stents (especially large numbers of stents)—including drug delivery stents. The process may be utilized used to apply primers, drug containing layers, and/or topcoats. The significance of this process is two-fold: this process simplifies the spray process and increases its reproducibility by virtue of being a simpler process. Additionally, since the stent is not contacted continuously at any one point, the issue of end ring defects should be reduced or essentially eliminated. It should also be noted that embodiments of the disclosed process maybe used on any drug eluting stent. Such coatings can be used on balloon expandable or self-expanding stents. The stent may be utilized in any part of the vasculature including neurological, carotid, coronary, renal, aortic, iliac, femoral, or other peripheral vasculature. There may also be no limitations on stent length, diameter, strut thickness, strut pattern, or stent material.

Implantable Devices

While the process detailed herein is often described with reference to coating a stent, it should be understood that the device or prosthesis coated in accordance with the embodiments of the present invention may be any suitable medical substrate that can be implanted in a human or veterinary patient. Examples of such implantable devices include stent-grafts, grafts (e.g., aortic grafts), artificial heart valves, cerebrospinal fluid shunts, anastomosis devices (e.g., AXIUS Coronary Shunt available from Guidant Corporation), pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGLOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. A polymeric implantable device should be compatible with the composition. The ethylene vinyl alcohol copolymer, however, adheres very well to metallic materials, more specifically to stainless steel.

Coating Substance

In an embodiment of the present invention, the coating substance may include a polymer dissolved in a fluid and optionally, an active agent added thereto. As a further option, the coating substance may include radiopaque elements, or radioactive isotopes.

Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid);

poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

In an embodiment of the present invention, the fluid in which the polymer is dissolved may comprise a solvent which may be defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

The embodiments of the composition may be prepared by conventional methods wherein all components are combined, then blended. For example, in an illustrative embodiment, a predetermined amount of an ethylene vinyl alcohol copolymer may be added to a predetermined amount of dimethyl acetamide (DMAC or DMAc). If necessary, heating, stirring and/or mixing can be employed to effect dissolution of the copolymer into the solvent—for example in an 80° C. water bath for one to two hours.

Active Agent

The active agent may be in true solution or saturated in the blended composition. If the active agent is not completely soluble in the composition, operations including mixing, stirring, and/or agitation can be employed to effect homogeneity of the residues. The active agent may be added in fine particles. The mixing of the active agent can be conducted at ambient pressure and at room temperature such that supersaturating the active ingredient is not desired. The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIIb/IIIa platelet membrane receptor antagonist antibody, recombinant hirudin, and thrombin inhibitors such as Angiomax a (Biogen, Inc., Cambridge, Mass.). Examples of such cystostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Application Process

In accordance with an embodiment of the present invention, the coating substance may be sprayed on to the stents utilizing a spray apparatus, such as, for example, an EFD 780S spray device with VALVEMATE 7040 control system (manufactured by EFD Inc., East Providence, R.I.). EFD spray device is an air-assisted external mixing atomizer. The composition is atomized into small droplets by air and uniformly applied to the stent surface. The atomization pressure can be maintained at a range of about 5 to 20 psi. The droplet size depends on such factors as viscosity of the solution, surface tension of the solvent, and atomizing pressure. Other types of spray applicators, including air-assisted internal mixing atomizers and ultrasonic applicators can also be used for the application of the composition.

The flow rate of the solution from the spray nozzle can be from about 0.01 mg/second to about 1.0 mg/second, for example about 0.1 mg/second. As an option, multiple repetitions for applying the composition can be performed, wherein each repetition is about 1 second to about 10 seconds, for example about 5 seconds, in duration. The amount of coating applied by each repetition can be about 0.1 micrograms/cm (of stent surface) to about 10 micrograms/cm, for example less than about 2 micrograms/cm per 5 second spray.

Each repetition can be followed by removal of a significant amount of the solvent(s). The removal of the solvent(s) can be performed following a waiting period of about 0.1 second to about 5 seconds after the application of the coating composition so as to allow the liquid sufficient time to flow and spread over the stent surface before the solvent(s) is removed to form a coating. The waiting period is particularly suitable if the coating composition contains a volatile solvent, such as solvents having boiling points>130° C. at ambient pressure, since such solvents are typically removed quickly.

Removal of the solvent(s) can be induced by the application of a gas or air. The application of a warm gas between each repetition prevents coating defects and minimizes interaction between the active agent and the solvent. Any suitable gas can be employed, examples of which include air or nitrogen. The temperature of the gas can be from about 15° C. to about 200° C. In one embodiment, for temperature stable drugs, the drying air temperature can be from ambient temperature up to about 100° C. and for drugs that are temperature sensitive, the temperature may be from ambient temperature up to about 50° C. The flow speed of the gas can be from about 0.5 feet$^3$/second (0.01 meters$^3$/second) to about 50 feet$^3$/second (1.42 meters$^3$/second), more narrowly about 2.5 feet$^3$/second (0.07 meters$^3$/second) to about 15 feet$^3$/second (0.43 meters$^3$/second). The gas can be applied for about 1 second to about 100 seconds, more narrowly for about 2 seconds to about 20 seconds. By way of example, warm gas applications can be performed at a temperature of about 60° C., at a flow speed of about 10 feet$^3$/second, and for about 10 seconds.

In one embodiment, the stent can be warmed to a temperature of from about 35° C. to about 80° C. prior to the application of the coating composition so as to facilitate faster removal of the solvent(s). The particular temperature selected depends, at least in part, on the particular active agent employed in the coating composition. By way of example, pre-heating of the stent prior to applying a composition containing actinomycin D should be performed at a temperature not greater than about 55° C. Pre-heating is particularly suitable for embodiments in which the solvent(s) employed in the coating composition has a high boiling point, i.e., volatile solvents having boiling points of, for example, >130° C. at ambient pressure (e.g., dimethylsulfoxide (DMSO), dimethylformamide (DMF), and dimethylacetamide (DMAC)).

Any suitable number of repetitions of applying the composition followed by removing the solvent(s) can be performed to form a coating of a desired thickness or weight. In embodiments in which the coating composition contains a volatile solvent, a waiting period of from about 0.1 second to about 20 seconds can be employed between solvent removal of one repetition and composition application of the subsequent repetition so as to ensure that the wetting rate of the coating composition is slower than the evaporation rate of the solvent within the composition, thereby promoting coating uniformity.

Coating Layers

To form an optional primer layer on the surface of the device, an embodiment of the composition free from any active agents is applied to the surface of the device. For the thermoplastic polymers, the composition could be exposed to a heat treatment at a temperature range of greater than about the glass transition temperature and less than about the melting temperature of the copolymer. The device should be exposed to the heat treatment for any suitable duration of time (e.g., 30 minutes) which would allow for the formation of the primer layer on the surface of the device and allows for the evaporation of the solvent. In the case of a stent made from a bioabsorbable or biostable polymer the stent could be exposed to a temperature at or above a glass transition temperature and less than a melting temperature for the polymer to improve the adherence of the substance to stent surfaces, wherein the stent would be exposed to the higher temperature while inside the chamber. The primer can be used for increasing the retention of a reservoir coating containing the active agent on the surface of the device, particularly metallic surfaces such as stainless steel. The primer can act as an intermediary adhesive tie layer between the surface of the device and the coating carrying the active agent—which, in effect, allows for the quantity of the active agent to be increased in the reservoir coating.

For the formation of the reservoir coating containing an active agent, an embodiment of the composition containing an active agent or combination of agents is applied to the device. If a primer layer is employed, the application should be performed subsequent to the drying of the primer layer.

An optional topcoat can be formed over the reservoir coating containing the active agents. An embodiment of the composition, free from any active agents, can be applied to the reservoir region subsequent to the drying of the reservoir region. The solvent is then allowed to evaporate, for example, by exposure to a selected temperature, to form the rate-limiting diffusion barrier.

For the reservoir coating containing the active agent and the optional top coat, a final heat treatment could be conducted to remove essentially all of the solvent(s) from the composition on the stent. The heat treatment can be conducted at about 30° C. to about 200° C. for about 15 minutes to about 16 hours, more narrowly at about 50° C. to about 100° C. for about 1 hour to about 4 hours. By way of example, the heat treatment can be conducted at about 75° C. for 1 hour. The temperature of exposure should not adversely affect the characteristics of the active agent or of the coating. The heating can be conducted in an anhydrous atmosphere and at ambient pressure. The heating can, alternatively, be conducted under a vacuum condition. It is understood that essentially all of the solvent(s) will be removed from the composition but traces or residues can remain blended in the coating.

Method of Use

A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of coating stents, comprising:

placing a plurality of stents in a chamber, the stents being made from a polymer;

forming a coating on surfaces of the polymer stents as the stents are being agitated and/or shaken within the chamber, the forming step including the steps of:

applying a composition to surfaces of the stents, and applying a heat treatment to the tumbling stents to aid drying of the composition on the stent surfaces including directing a gaseous compound over the agitating and/or shaking stents, wherein the heat treatment exposes the composition to a temperature range of greater than about the glass transition temperature and less than the melting temperature of the composition.

2. The method of claim 1, wherein the applying a composition includes atomizing the composition into small droplets by gas and uniformly applying the atomized composition on the stents.

3. The method of claim 1, further comprising repeating the applying a composition and applying a heat treatment steps.

4. The method of claim 1 wherein the stents are agitated and/or shaken within the chamber by rotating the chamber about an acute axis so that the stents tumble within the chamber.

5. The method of claim 1, further including the step of warming the stents before the applying a composition step to increase the removal rate for a solvent.

6. The method of claim 1, wherein the stents contact each other and/or walls of the chamber during the forming a coating step.

7. The method of claim 1, wherein the coating is a primer layer comprising a polymer free from active agents.

8. The method of claim 7, further including the step of forming a second coating comprising an active agent subsequent to drying of the primer layer.

* * * * *